(12) United States Patent
Springer et al.

(10) Patent No.: US 6,696,582 B2
(45) Date of Patent: Feb. 24, 2004

(54) METHOD FOR PRODUCING ALIPHATIC CARBOXYLIC ACIDS FROM ALDEHYDES

(75) Inventors: Helmut Springer, Dinslaken (DE); Peter Heymanns, Essen (DE)

(73) Assignee: Celanese Chemicals Europe GmbH (DE)

( * ) Notice: Subject to any disclaimer, the term of this patent is extended or adjusted under 35 U.S.C. 154(b) by 22 days.

(21) Appl. No.: 10/204,286

(22) PCT Filed: Feb. 21, 2001

(86) PCT No.: PCT/EP01/01946
§ 371 (c)(1),
(2), (4) Date: Sep. 10, 2002

(87) PCT Pub. No.: WO01/66505
PCT Pub. Date: Sep. 13, 2001

(65) Prior Publication Data
US 2003/0100793 A1 May 29, 2003

(30) Foreign Application Priority Data
Mar. 4, 2000 (DE) .......................................... 100 10 769

(51) Int. Cl.$^7$ ................................................ C07C 51/16
(52) U.S. Cl. ........................................ 554/134; 554/132
(58) Field of Search ................................. 554/134, 132

(56) References Cited

FOREIGN PATENT DOCUMENTS

| | | | |
|---|---|---|---|
| DE | 1154454 | | 9/1963 |
| DE | 1154454 | * | 9/1968 |

* cited by examiner

*Primary Examiner*—Deborah Carr
(74) *Attorney, Agent, or Firm*—Muserlian, Lucas and Mercanti

(57) ABSTRACT

The invention relates to a method for producing aliphatic carboxylic acids from aldehydes by means of oxidation with oxygen or gases containing oxygen. This novel process is carried out in at least two stages at different temperatures, preferably in the absence of catalysts.

16 Claims, No Drawings

METHOD FOR PRODUCING ALIPHATIC CARBOXYLIC ACIDS FROM ALDEHYDES

This application is a 371 of PCT/EP01/01946 filed Feb. 21, 2001.

The present invention relates to a novel, noncatalytic process for preparing aliphatic carboxylic acids from aldehydes by oxidation with oxygen or oxygen-containing gases.

Aldehydes are the customary starting materials for obtaining carboxylic acids. The preference for aldehydes for this area of use derives from their manifold availability and the easy oxidative conversion of the carbonyl group into the carboxyl group. In processes applied industrially, the conversion of aldehydes to carboxylic acids mainly takes/place in the presence of catalysts. However, processes in which the use of catalysts is dispensed with are also known. To avoid side reactions, both the catalytic and the noncatalytic processes employ temperatures which are as low as possible, and in general the reaction temperature does not exceed 100° C. Suitable catalysts are mainly salts of transition metals, in particular salts of cobalt and of manganese, and of chromium, iron, copper, nickel, silver and vanadium. The formation of carboxylic acids from aldehydes is frequently associated, even if optimal temperature conditions are maintained, with side reactions and degradation reactions. This applies equally to reactions in the presence and in the absence of catalysts. In such cases, the selectivity of the conversion can be considerably improved by adding alkali metal salts of weak acids to the reactants. However, the disadvantage of this variant of the process is that the salts have an inhibitory effect, so that the reaction time must be extended for complete conversion of the starting materials.

In the process described in DE-A 30 29 700, the appropriate aldehydes for preparing aliphatic monocarboxylic acids having 6 to 9 carbon atoms are oxidized with oxygen in pure form or with air. A combination of manganese and copper compounds which are soluble in the acid acts as catalyst, the molar ratio of manganese to copper being in the range from 5:1 to 0.5:1. The conversion of the starting materials takes place in liquid phase at temperatures of about 50 to 80° C. and pressures in the range from about 1.4 to 10.3 bar. The main difficulty of this process is described, in the description of the process, as being the presence of copper compounds, and manganese compounds, in the reaction product, i.e. in the carboxylic acid. Elaborate purification measures are necessary to remove the metals, for example precipitation thereof with aqueous oxalic acid.

The process disclosed in U.S. Pat. No. 4,487,720 for preparing $C_5$ to $C_9$ monocarboxylic acids by oxidizing aldehydes with the same number of carbon atoms using pure oxygen or air likewise operates with copper and manganese compounds as catalysts. The disadvantage described for this procedure is the formation of copper films which appear on purification of the acid by distillation and result in mechanical damage to the distillation apparatus. To avoid this problem, it is recommended that the distillation be carried out in the presence of oxygen.

Another catalytic process for reacting aldehydes with oxygen to form carboxylic acids is disclosed in the published international application WO 97/14668. The catalysts used are substituted or unsubstituted alkylamines, alkylamine N-oxides, aromatic amines, aromatic N-oxides, heterocyclic amines, heterocyclic amine N-oxides and mixtures thereof. It is expressly pointed out that the nitrogen compounds with catalytic activity must have a higher boiling point than the product of the reaction in order to suppress contamination of the acid by the catalyst.

According to the teaching of the published Japanese patent application 53-105413, α-branched aliphatic aldehydes are oxidized with oxygen in the presence of lithium or alkaline earth metal compounds, which are employed in amounts of from 0.01 to 10% by weight (based on the complete reaction system), in order to prepare α-branched aliphatic carboxylic acids.

The procedure described in the French patent application 2 769 624 is characterized by maintaining low reaction temperatures, namely temperatures between 0 and 25° C. The process likewise requires the presence of alkali metal or alkaline earth metal compounds as catalysts which possibly increase the reaction rate at the mild temperatures which are to be maintained. This is because long reaction times not only are prohibited for economic reasons but may also lead to unwanted side reactions.

DE 29 31 154 C2 discloses the preparation of aliphatic carboxylic acids with 4 to 10 carbon atoms by oxidation of the corresponding aldehydes with oxygen or oxygen-containing gases in the presence of the complex anion $[Fe(CN)_5H_2O]^{3-}$ as catalyst. The thermal instability of the anion restricts the reaction temperature to a range from 20 to 50° C.

Mixtures of isomeric branched aliphatic or cycloaliphatic carboxylic acids are obtained by the procedure of German patent 1 154 454 from aldehydes which are oxidized in a thin liquid layer at a temperature of 65 to 110° C. with an oxygen-containing gas without use of catalysts. The reaction is carried out in tubes which are empty or packed with inert materials with a large surface area. The proportion of acid in the product of the reaction is between 59 and 80%.

The known processes for preparing carboxylic acids from aldehydes do not yet meet all the technical and economic requirements for modern processes used industrially. The use of catalysts is associated with elaborate purification steps, to which the product of the reaction must be subjected in order to obtain carboxylic acids which can be processed further without problems. Noncatalytic processes are frequently unsatisfactory in terms of the conversion and selectivity for the required product.

The object therefore was to develop a procedure which avoids the disadvantages mentioned and makes it possible to obtain carboxylic acids from aldehydes in high yield with acceptable technical complexity.

This object is achieved by a process for preparing aliphatic carboxylic acids having 4 to 10 carbon atoms by oxidation of the corresponding aldehydes with oxygen or oxygen-containing gases. The process comprises carrying out the oxidation in the temperature range from 0 to 100° C. in at least two stages, with the temperatures increasing from stage to stage.

Deliberate management of the temperature makes it possible to carry out the oxidation of aldehydes to carboxylic acids with oxygen in pure form or as a constituent of gas mixtures, with high conversion, very selectively and without use of catalysts. In this connection, reference must be made in particular to the fact that low reaction temperatures, i.e. temperatures up to about 40° C., lead to unsatisfactory conversions, whereas higher reaction temperatures, i.e. temperatures above about 40° C., distinctly impair the selectivity of the reaction. In these circumstances, it was not to be expected that combining ranges of lower and higher reaction temperature does not lead to a cumulation of the unwanted results but, on the contrary, optimizes both the conversion and the selectivity. It is also noteworthy that the use of different temperatures during the reaction effectively suppresses the formation of peroxy compounds, which may induce uncontrolled oxidation reactions and thus impair the selectivity of the reaction and, moreover, because they are able to decompose easily also require special safety measures.

A very essential feature of the procedure of the invention is the choice of the temperature range in which the reaction takes place, and the control of the changes in temperature during the reaction within this range. It has proved suitable to oxidize the aldehydes in the novel process at temperatures between 0 and 100° C., preferably between 20 and 100° C. and, in particular, between 40 and 80° C. In contrast to previous practice, the reaction is carried out not at a constant temperature or a temperature which is approximately constant within technical possibilities, but in a plurality of stages. The stages differ from one another in such a way that the temperature increases, i.e. is higher in the following stage than in the preceding one. The number of stages can in principle be chosen without restriction and can therefore be adapted individually to the material characteristics of the starting aldehydes, e.g. their reactivity, their stability under the reaction conditions, but also their purity if this feature influences the course of the reaction. The aldehyde oxidation normally takes place according to the invention in two to four stages. However, it is also possible to implement processes with more than four stages, although such embodiments are restricted to special cases in view of the greater complexity of the apparatus. It is generally sufficient to design the novel process as two-stage process, i.e. to carry out the reaction of the reactants at two temperatures.

The temperature difference between two consecutive stages depends, apart from the nature of the starting material, essentially on two factors, the initial temperature, i.e. the temperature in the first reaction stage, and the total number of stages. A lower initial temperature means that a larger temperature difference is possible for a given number of stages. Thus, it has proved suitable, for example, in the two-stage procedure with an initial temperature of 40° C. to maintain a temperature of 60 to 70° C. in the subsequent stage, and with an initial temperature of 50° C. to allow the reaction in the second stage to take place at 65 to 75° C. In processes with three or more/stages, the temperature difference between adjacent stages is correspondingly less, and may be between 5 and 20° C., preferably 10 to 15° C. The temperature data mentioned are merely guideline values which should be adjusted to the specific circumstances of the individual case. If more than two reaction stages are used, it is unnecessary to maintain identical temperature differences between the individual stages. On the contrary, variable temperature differences can be chosen and be made appropriate for individual requirements.

The hold-up time of the aldehydes in the individual stages of the multistage process depends on the chosen reaction temperature. It is generally true that from 40 to 90% by weight of the aldehyde employed is reacted at temperatures up to 40° C. and the remainder is reacted at temperatures up to 100° C., preferably up to 80° C. It is possible, as described above, to provide further reaction stages within the ranges characterized by the maximum temperatures specified above. Accordingly, for example, in a three-stage reaction there may be a sequence of two stages at temperatures up to 40° C. and one stage up to 100° C. or preferably 80° C. It is likewise possible to react part of the aldehyde to the carboxylic acid in a temperature stage extending up to a maximum of 40° C., and to oxidize the remaining aldehyde in two stages up to 100° C., preferably 80° C. A procedure with four or more stages is managed correspondingly. The reaction is preferably carried out under atmospheric pressure. The use of elevated pressure is not, however, precluded. The working range is normally from atmospheric pressure to 1.0 MPa, preferably atmospheric pressure to 0.8 MPa.

The reaction time needed to convert aldehydes into carboxylic acids by the process of the invention depends inter alia on the reaction temperature, the nature of the starting materials and the/ratio of the amounts of the reactants. It is normally from 30 min to 20 h, in particular 3 to 8 h.

The novel process is centered on the oxidation of unbranched and branched $C_4$ to $C_{10}$ aldehydes, preferably of unbranched aldehydes of said molecule size. The origin of the aldehydes is not restricted to particular preparation processes. Aldehydes obtained by oxo process, i.e. by reacting $C_3$ to $C_9$ olefins with carbon monoxide and hydrogen, are preferred because of their ready availability. It is immaterial in this connection which specific embodiment of the oxo process was used to obtain the aldehydes, i.e. whether the reaction was catalyzed, for example, by cobalt or by rhodium, whether the metals were employed alone or together with complexing agents, and the catalyst was homogeneously dissolved in the reaction mixture or formed a separate heterogeneous phase.

The oxidizing agent used in the process of the invention is molecular oxygen or gas mixtures containing molecular oxygen. Other constituents of such gas mixtures are inert gases, for example nitrogen, noble gases and carbon dioxide. The proportion of inert constituents in the oxygen-containing gas mixture is up to 90% by volume, in particular 30 to 80% by volume. The preferred oxidizing agents are oxygen or air.

The aldehydes can be employed as such or dissolved in a solvent which is inert under the reaction conditions. Examples of suitable solvents are ketones such as acetone, esters, for example ethyl acetate, hydrocarbons, for example toluene, and nitrohydrocarbons such as nitrobenzene. The concentration of the aldehyde is limited by its solubility in the solvent.

The process of the invention can be carried out batchwise or continuously. Recycling of unreacted reactants is possible in both cases. In a batchwise reaction the temperature stages are achieved by increasing the temperature in the same reactor after a predetermined partial conversion is reached (corresponding to a predetermined temperature/time program). On management of the process continuously the reaction mixture will be fed, likewise after reaching specified partial conversions (or in accordance with a predetermined temperature/time program), into two or more reactors arranged as cascade and having different temperatures.

In a proven embodiment of the process of the invention, the aldehyde is placed in a suitable reactor, for example a tubular reactor which is provided with a distributor plate and optionally also contains packings, and the oxygen or the oxygen-containing gas mixture is passed upwards through the aldehyde.

In another embodiment, the reactor used is a trickle tower containing packings. The aldehyde is allowed to trickle down over the packing and, at the same time, oxygen or an oxygen-containing gas mixture is passed cocurrently or countercurrently into the tower.

The following examples describe the preparation of n-pentanoic acid, n-heptanoic acid and n-nonanoic acid by the process of the invention. The reaction takes place in two stages which differ in the reaction temperature maintained in each. The examples are compared with the results of comparative tests carried out in one stage in each case at the lower or higher temperature of the two-stage procedure. The experimental data include the weight of oxidation product (crude acid); this value correlates with the conversion;

the active oxygen content in the reaction product; this means oxygen in the form of peracids; for safety reasons, the peracid content in the reaction product should be minimized;

GC analysis of the crude acid; the forerun and after-run components are not subdivided but combined under the terms low boilers and high boilers;

the aldehyde conversion; if isomer-containing mixtures are used, only the straight-chain aldehydes are taken into account;

the selectivity, i.e. the amount of carboxylic acid in the reaction product relative to reacted aldehyde.

The novel process is, of course, not confined to the embodiments described hereinafter.

EXAMPLES

Preparation of n-pentanoic Acid

Comparative Examples 1 and 2

The liquid-phase oxidation of n-pentanal to n-pentanoic acid was carried out without added catalyst in a glass bubble column reactor with an internal diameter of 38 mm and a length of 150 cm. Depending on the behavior of the reaction, external cooling or heating of the reactor was provided by a water circulation connected to a heat exchanger, and the internal temperature was kept constant in this way. The oxygen was fed in from below through a glass filter plate which had a maximum pore width of 16–40 µm and was connected to the bubble column.

In each of the oxidations, 800.0 g of n-pentanal of the following composition determined by gas chromatography analysis were employed:

| | |
|---|---|
| 0.42% | low boilers |
| 99.07% | n-pentanal |
| 0.29% | n-pentanoic acid |
| 0.22% | high boilers |

The results after an oxidation time of 6 hours were as follows:

TABLE 1

| Reaction temperature (° C.) | Comparative example 1<br>40 | Comparative example 2<br>60 |
|---|---|---|
| Weight of oxidation product (g) | 931.0 | 935.7 |
| Active oxygen content (g/kg) | 0.84 | 1.04 |
| GC analysis (%): | | |
| Low boilers | 0.31 | 0.46 |
| n-Pentanal | 5.69 | 1.49 |
| n-Pentanoic acid | 93.21 | 96.77 |
| High boilers | 0.79 | 1.28 |
| n-Pentanal conversion (% of theory) | 93.3 | 98.2 |
| Selectivity for n-pentanoic acid (% of theory) | 99.3 | 98.7 |

Example 1

This test was carried out under the conditions of comparative examples 1 and 2 with the difference that the reaction temperature was altered during the oxidation. At the start of the reaction the temperature was kept constant at 40° C. for 4 hours, and it was then adjusted to 60° C. for 2 hours.

800.0 g of n-pentanal of the composition mentioned in comparative examples 1 and 2 were employed in the oxidation.

The results after completion of the oxidation (total reaction time 6 hours) were as follows:

| Reaction temperature (° C.) | |
|---|---|
| 1st hour | 40 |
| 2nd hour | 40 |
| 3rd hour | 40 |
| 4th hour | 40 |
| 5th hour | 60 |
| 6th hour | 60 |
| Weight of oxidation product (g) | 936.9 |
| Active oxygen content (g/kg) | 0.50 |
| GC analysis (%): | |
| Low boilers | 0.29 |
| n-Pentanal | 1.48 |
| n-Pentanoic acid | 97.35 |
| High boilers | 0.88 |
| n-Pentanal conversion (% of theory) | 98.2 |
| Selectivity for n-pentanoic acid (% of theory) | 99.3 |

Preparation of n-heptanoic Acid

Comparative Examples 3 and 4

The liquid-phase oxidation of n-heptanal to n-heptanoic acid was carried out without added catalyst in a glass bubble column reactor with an internal diameter of 38 mm and a length of 150 cm. Depending on the behavior of the reaction, external cooling or heating of the reactor was provided by a water circulation connected to a heat exchanger, and the internal temperature was kept constant in this way. The oxygen was fed in from below through a glass filter plate which had a maximum pore width of 16–40 µm and was connected to the bubble column.

In each of the oxidations, 800.0 g of n-heptanal of the following composition determined by gas chromatography analysis were employed:

| | |
|---|---|
| 0.62% | low boilers |
| 97.74% | n-heptanal |
| 0.10% | n-heptanoic acid |
| 1.54% | high boilers |

The results after an oxidation time of 6 hours were as follows:

TABLE 2

| Reaction temperature (° C.) | Comparative example 3<br>50 | Comparative example 4<br>70 |
|---|---|---|
| Weight of oxidation product (g) | 899.2 | 902.9 |
| Active oxygen content (g/kg) | 0.71 | 1.54 |
| GC analysis (%): | | |
| Low boilers | 0.82 | 1.12 |
| n-Heptanal | 5.42 | 2.15 |
| n-Heptanoic acid | 91.79 | 94.05 |
| High boilers | 1.97 | 2.68 |

TABLE 2-continued

|  | Comparative example 3 | Comparative example 4 |
|---|---|---|
| Reaction temperature (° C.) | 50 | 70 |
| n-Heptanal conversion (% of theory) | 93.8 | 97.5 |
| Selectivity for n-Heptanoic acid (% of theory) | 98.9 | 97.7 |

Example 2

This test was carried out under the conditions of comparative examples 3 and 4 with the difference that the reaction temperature was altered during the oxidation. At the start of the reaction the temperature was kept constant at 50° C. for 4 hours, and it was then adjusted to 70° C. for 2 hours.

800.0 g of n-heptanal of the composition mentioned in comparative examples 3 and 4 were employed in the oxidation.

The results after completion of the oxidation (total reaction time 6 hours) were as follows:

| Reaction temperature (° C.) | |
|---|---|
| 1st hour | 50 |
| 2nd hour | 50 |
| 3rd hour | 50 |
| 4th hour | 50 |
| 5th hour | 70 |
| 6th hour | 70 |
| Weight of oxidation product (g) | 902.6 |
| Active oxygen content (g/kg) | 0.87 |
| GC analysis (%): | |
| Low boilers | 0.84 |
| n-Heptanal | 2.20 |
| n-Heptanoic acid | 94.85 |
| High boilers | 2.11 |
| n-Heptanal conversion (% of theory) | 97.5 |
| Selectivity for n-heptanoic acid (% of theory) | 98.8 |

Preparation of n-nonanoic Acid

Comparative examples 5 and 6

The liquid-phase oxidation of n-nonanal to n-nonanoic acid was carried out without added catalyst in a glass bubble column reactor with an internal diameter of 38 mm and a length of 150 cm. Depending on the behavior of the reaction, external cooling or heating of the reactor was provided by a water circulation connected to a heat exchanger, and the internal temperature was kept constant in this way. The oxygen was fed in from below through a glass filter plate which had a maximum pore width of 16–40 μm and was connected to the bubble column.

In each of the oxidations, 800.0 g of n-nonanal of the following composition determined by gas chromatography analysis were employed:

| 0.19% | low boilers |
|---|---|
| 9.61% | isononanal |
| 89.56% | n-nonanal |
| 0.04% | isononanoic acid |
| 0.25% | n-nonanoic acid |
| 0.35% | high boilers |

The results after an oxidation time of 6 hours were as follows:

TABLE 3

|  | Comparative example 5 | Comparative example 6 |
|---|---|---|
| Reaction temperature (° C.) | 50 | 70 |
| Weight of oxidation product (g) | 880.4 | 883.4 |
| Active oxygen content (g/kg) | 0.71 | 1.61 |
| GC analysis (%): | | |
| Low boilers | 0.40 | 1.10 |
| Isononanal | 1.44 | 1.04 |
| n-Nonanal | 7.27 | 2.88 |
| Isononanoic acid | 8.15 | 7.90 |
| n-Nonanoic acid | 81.78 | 85.44 |
| High boilers | 0.96 | 1.64 |
| n-Nonanal conversion (% of theory) | 91.1 | 96.4 |
| Selectivity for n-nonanoic acid (% of theory) | 98.9 | 98.0 |

Example 3

This test was carried out under the conditions of comparative examples 5 and 6 with the difference that the reaction temperature was altered during the oxidation. At the start of the reaction the temperature was kept constant at 50° C. for 4 hours, and it was then adjusted to 70° C. for 2 hours.

800.0 g of n-nonanal of the composition mentioned in comparative examples 5 and 6 were employed in the oxidation.

The results after completion of the oxidation (total reaction time 6 hours) were as follows:

| Reaction temperature (° C.) | |
|---|---|
| 1st hour | 50 |
| 2nd hour | 50 |
| 3rd hour | 50 |
| 4th hour | 50 |
| 5th hour | 70 |
| 6th hour | 70 |
| Weight of oxidation product (g) | 884.0 |
| Active oxygen content (g/kg) | 0.79 |
| GC analysis (%): | |
| Low boilers | 0.41 |
| Isononanal | 1.00 |
| n-Nonanal | 3.17 |
| Isononanoic acid | 8.74 |
| n-Nonanoic acid | 85.96 |
| High boilers | 0.72 |
| n-Nonanal conversion (% of theory) | 96.1 |
| Selectivity for n-nonanoic acid (% of theory) | 99.0 |

Example 4

This test was carried out under the conditions of comparative examples 5 and 6 with the difference that the reaction temperature was altered during the oxidation. At the start of the reaction the temperature was kept constant at 50° C. for 5 hours, and it was then adjusted to 70° C. for 1 hour.

800.0 g of n-nonanal of the composition mentioned in comparative examples 5 and 6 were employed in the oxidation.

The results after completion of the oxidation (total reaction time 6 hours) were as follows:

| Reaction temperature (° C.) | |
| --- | --- |
| 1st hour | 50 |
| 2nd hour | 50 |
| 3rd hour | 50 |
| 4th hour | 50 |
| 5th hour | 50 |
| 6th hour | 70 |
| Weight of oxidation product (g) | 884.8 |
| Active oxygen content (g/kg) | 1.05 |
| GC analysis (%): | |
| Low boilers | 0.20 |
| Isononanal | 1.24 |
| n-Nonanal | 4.67 |
| Isononanoic acid | 8.67 |
| n-Nonanoic acid | 84.39 |
| High boilers | 0.83 |
| n-Nonanal conversion (% of theory) | 94.2 |
| Selectivity for n-nonanoic acid (% of theory) | 99.0 |

Example 5

This test was carried out under the conditions of comparative examples 5 and 6 with the difference that the reaction temperature was altered during the oxidation. At the start of the reaction the temperature was kept constant at 50° C. for 3 hours, and it was then adjusted to 70° C. for 3 hours.

800.0 g of n-nonanal of the composition mentioned in comparative examples 1 and 2 were employed in the oxidation.

The results after completion of the oxidation (total reaction time 6 hours) were as follows:

| Reaction temperature (° C.) | |
| --- | --- |
| 1st hour | 50 |
| 2nd hour | 50 |
| 3rd hour | 50 |
| 4th hour | 70 |
| 5th hour | 70 |
| 6th hour | 70 |
| Weight of oxidation product (g) | 886.8 |
| Active oxygen content (g/kg) | 1.08 |
| GC analysis (%): | |
| Low boilers | 0.17 |
| Isononal | 0.99 |
| n-Nonanal | 2.83 |
| Isononanoic acid | 8.75 |
| n-Nonanoic acid | 86.14 |
| High boilers | 1.12 |
| n-Nonanal conversion (% of theory) | 96.5 |
| Selectivity for n-nonanoic acid (% of theory) | 98.9 |

What is claimed is:

1. A process for preparing aliphatic carboxylic acids having 4 to 10 carbon atoms by oxidation of the corresponding aldehydes with oxygen or oxygen-containing gases, wherein the oxidation takes place in the temperature range from 0 to 100° C. in at least two stages, with the temperature increasing from stage to stage.

2. The process as claimed in claim 1, wherein the oxidation takes place at temperatures of from 20 to 100° C.

3. The process as claimed in claim 1, wherein the oxidation takes place in two to four stages.

4. The process of claim 1, wherein a two-staged procedure, a temperature of 40° is maintained in the first stage, and a temperature of 60 to 70° C. is maintained in the second stage.

5. The process of claim 1, wherein in a two-staged procedure, a temperature of 50° C. is maintained in the first stage, and a temperature of 65 to 75° C. is maintained in the second stage.

6. The process of claim 1, wherein the temperature difference between adjacent temperature stages is 5 to 20° C.

7. The process of claim 1, wherein 40 to 90% by weight of the aldehyde employed are reacted at temperatures up to 40° C., and the remainder is reacted at temperatures up to 100° C.

8. The process of claim 1, wherein the oxidation takes place in the range from atmospheric pressure to 1.0 MPa.

9. The process of claim 1, wherein the oxidizing agent is molecular oxygen.

10. The process of claim 1, wherein the oxidizing agent is a gas mixture comprising molecular oxygen and up to 90% by volume of inert gases.

11. The process as claimed in claim 10, wherein the gas mixture is air.

12. The process of claim 3 wherein the oxidation takes place in two stages.

13. The process of claim 6 wherein the temperature difference between adjacent temperature stages is 10 to 15° C.

14. The process of claim 7 wherein the remainder is heated up to 80° C.

15. The process of claim a wherein the oxidation is effected from atmospheric pressure up to 0.8 MPa.

16. The process of claim 10 wherein the oxidizing agent contains 30 to 80% by volume of insert gases.

\* \* \* \* \*